United States Patent
Davis et al.

[11] Patent Number: 6,019,782
[45] Date of Patent: Feb. 1, 2000

[54] DISPOSABLE THERMAL BODY PAD

[75] Inventors: Leane Kristine Davis, Milford; Ronald Dean Cramer; William Robert Ouellette, both of Cincinnati; Dawn Michele Kimble, Sharonville, all of Ohio

[73] Assignee: The Procter & Gamble Company, Cincinnati, Ohio

[21] Appl. No.: 08/984,367

[22] Filed: Dec. 3, 1997

Related U.S. Application Data

[63] Continuation-in-part of application No. 08/777,856, Dec. 31, 1996.

[51] Int. Cl.⁷ ........................................ A61F 7/00
[52] U.S. Cl. ............................ 607/96; 607/108; 607/112
[58] Field of Search ........................... 607/104, 108–112, 607/114; 165/46; 126/204; 602/2; 62/4; 264/53

[56] References Cited

U.S. PATENT DOCUMENTS

| | | |
|---|---|---|
| Re. 32,026 | 11/1985 | Yamashita et al. ............... 126/263 |
| 2,547,886 | 4/1951 | Poux ................................. 62/1 |
| 2,562,121 | 7/1951 | Poux ............................... 150/2.2 |
| 2,602,302 | 7/1952 | Poux ................................. 62/1 |
| 3,463,161 | 8/1969 | Andrassy ......................... 128/402 |
| 3,900,035 | 8/1975 | Welch et al. .................... 128/402 |
| 4,095,583 | 6/1978 | Petersen et al. ................. 126/263 |
| 4,106,477 | 8/1978 | Feld . | |
| 4,205,685 | 6/1980 | Yoshida et al. ................. 128/399 |
| 4,255,157 | 3/1981 | Yamaguchi et al. ............. 44/3 C |
| 4,268,272 | 5/1981 | Taura ................................ 44/3 R |
| 4,282,005 | 8/1981 | Sato et al. ........................ 44/3 R |
| 4,366,804 | 1/1983 | Abe ................................. 126/263 |
| 4,516,564 | 5/1985 | Koiso et al. .................... 126/263 |
| 4,522,190 | 6/1985 | Kuhn et al. ..................... 126/263 |
| 4,575,097 | 3/1986 | Brannigan et al. .............. 128/402 |
| 4,649,895 | 3/1987 | Yasuki et al. ................... 126/263 |

(List continued on next page.)

FOREIGN PATENT DOCUMENTS

| | | |
|---|---|---|
| 0 370 600 A1 | 7/1989 | European Pat. Off. .......... F24J 1/00 |
| 160443 | 9/1983 | India ............................... C09K 3/02 |
| 56-145846 | 11/1981 | Japan ............................. A61F 7/03 |
| 57-170252 | 10/1982 | Japan ............................. A61F 7/03 |
| 58-37075 | 3/1983 | Japan ............................. C09K 5/00 |
| 3-100090 | 4/1991 | Japan ............................. C09K 5/00 |
| 5-317188 | 12/1993 | Japan ............................. A47J 36/28 |
| 6-1969 | 1/1994 | Japan ............................. C09K 5/00 |
| 6-315498 | 11/1994 | Japan ............................. A61F 7/08 |
| 6-343658 | 12/1994 | Japan ............................. A61F 7/08 |
| 7-67907 | 3/1995 | Japan ............................. A61F 7/08 |
| 7-112006 | 5/1995 | Japan ............................. A61F 7/08 |
| 7-124192 | 5/1995 | Japan ............................. A61F 7/08 |
| 7-49042 | 5/1995 | Japan ............................. A61F 7/08 |
| 7-194641 | 8/1995 | Japan ............................. A61F 7/08 |
| 7-194642 | 8/1995 | Japan ............................. A61F 7/08 |
| 8-80317 | 3/1996 | Japan ............................. A61F 7/08 |
| 8-98856 | 4/1996 | Japan ............................. A61F 7/08 |
| 8-126656 | 5/1996 | Japan ............................. A61F 7/08 |
| 2 205 496 | 12/1988 | United Kingdom ............. A61F 7/03 |
| 2 297 490 | 8/1996 | United Kingdom ............. A61F 7/03 |
| WO 94/00087 | 1/1994 | WIPO ............................. A61F 7/00 |

*Primary Examiner*—Cary O'Connor
*Assistant Examiner*—Ryan Carter
*Attorney, Agent, or Firm*—Loy M. White; T. David Reed; Douglas C. Mohl

[57] ABSTRACT

The present invention relates to disposable thermal body pads comprising one or more thermal packs having a unified structure of at least one continuous layer of a semirigid material which softens when heated and a plurality of individual heat cells, spaced apart and fixed within or to the unified structure of the thermal pack. The disposable thermal body pads are intended to be attached to a user's clothing on one side and to be held directly against the user's skin on the other side. More particularly, the present invention relates to disposable thermal body pads having good conformity to user's body which provides consistent, convenient and comfortable heat application. Even more particularly, the present invention relates to such disposable thermal body pads intended for relieving menstrual pain.

50 Claims, 2 Drawing Sheets

U.S. PATENT DOCUMENTS

| | | | |
|---|---|---|---|
| 4,756,299 | 7/1988 | Podella | 126/263 |
| 4,860,748 | 8/1989 | Chiurco et al. | 128/399 |
| 4,886,063 | 12/1989 | Crews | 128/403 |
| 4,925,743 | 5/1990 | Ikeda et al. | 428/702 |
| 4,995,126 | 2/1991 | Matsuda | 5/421 |
| 5,025,777 | 6/1991 | Hardwick | 126/263 |
| 5,046,479 | 9/1991 | Usui | 126/204 |
| 5,062,269 | 11/1991 | Siegel | 62/4 |
| 5,125,392 | 6/1992 | Hardwick | 126/263 |
| 5,179,944 | 1/1993 | McSymtz | 128/403 |
| 5,190,033 | 3/1993 | Johnson | 128/403 |
| 5,233,981 | 8/1993 | Miyashita | 607/114 |
| 5,342,412 | 8/1994 | Ueki | 607/114 |
| 5,366,491 | 11/1994 | Ingram et al. | 607/108 |
| 5,366,492 | 11/1994 | Ueki | 607/114 |
| 5,405,671 | 4/1995 | Kamin et al. | 428/69 |

DISPOSABLE THERMAL BODY PAD

CROSS REFERENCE TO RELATED APPLICATION

This application is a continuation-in-part of application Ser. No. 08/777,856, filed Dec. 31, 1996.

TECHNICAL FIELD

The present invention relates to disposable thermal body pads comprising one or more thermal packs having a unified structure of at least one continuous layer, preferably of a semirigid material which softens when heated, and a plurality of individual heat cells spaced apart and fixed within or to the unified structure of the thermal pack. The disposable thermal body pads are intended to be attached to a user's clothing on one side and to be held directly against the user's skin on the other side. More particularly, the present invention relates to disposable thermal body pads having good conformity to user's body which provides consistent, convenient and comfortable heat application. Even more particularly, the present invention relates to such disposable thermal body pads intended for relieving body pain, preferably menstrual pain.

BACKGROUND OF THE INVENTION

A common method of treating acute, recurrent, and/or chronic pain is by the topical application of heat to the afflicted area. Such heat treatments are used as a means of therapy for conditions which include aches, stiffness in muscles and joints, nerve pain, rheumatism and the like. Typically, the method for relieving pain using heat treatments has been to topically apply a relatively high heat, i. e., greater than about 40° C., for a short period of time, i. e., from about twenty minutes to about one hour. These treatments include the use of whirlpools, hot towels, hydrocollators, hot water bottles, hot packs, heating pads and elastic compression bands. Many of these devices employ reusable thermal packs containing, e.g., water and/or microwaveable gels. In general, most of these devices are inconvenient to use on a regular and extended basis because the heat energy may not be immediately available when needed or released in a controllable manner. That is, many of these thermal units or devices do not provide long lasting heat and also do not maintain a consistent temperature over long periods of time. Proper positioning of the thermal energy also may not be maintainable during use. The beneficial therapeutic effects from this administration of heat diminish after the heat source is removed.

The present inventors, however, have discovered that maintaining a sustained skin temperature of from about 32° C. to about 50° C., preferably from about 32° C. to about 45° C., more preferably from about 32° C. to about 42° C., most preferably from about 32° C. to about 39° C., still most preferably from about 32° C. to about 37° C., for a period of from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved without any adverse events, such as skin burns which may be incurred by using a high temperature for a long period of time, substantially relieves acute, recurrent, and/or chronic pain, including skeletal, muscular, and/or referred pain, of a person having such pain.

The present inventors have further discovered that preferably maintaining a sustained skin temperature of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, substantially relieves acute, recurrent, and/or chronic back pain, including skeletal, muscular, and/or referred back pain, of a person having such pain and substantially prolongs relief even after the heat source is removed from the afflicted body part.

Disposable heat packs based on iron oxidation, such as those described in U.S. Pat. Nos. 4,366,804, 4,649,895, 5,046,479 and Re. 32,026, are known. However, such devices have proven not totally satisfactory because many of these devices are bulky, cannot maintain a consistent and controlled temperature, and have unsatisfactory physical dimensions, which hinder their effectiveness. Specifically, such devices cannot be easily incorporated into pads which can comfortably conform to various body contours, and hence, they deliver short duration, inconsistent, inconvenient and/or uncomfortable heat application directly to the body.

The present inventors have developed disposable thermal body pads comprising one or more thermal packs having a unified structure, wherein each thermal pack comprises at least one continuous layer, preferably of a semirigid material, which is semirigid in specific areas of the thermal pack, yet which softens in between such areas when heated during use, most preferably comprising a coextruded material of polypropylene and ethylene vinyl acetate (EVA). The body pads also comprise a plurality of individual heat cells, which typically comprise an exothermic composition, preferably comprising a specific iron oxidation chemistry, and have specific physical dimensions and fill characteristics, spaced apart and fixed along the thermal pack. Active heat cells, that is, heat cells having a temperature of about 35° C. or greater, preferably soften narrow portions of the continuous layer or layers of semirigid material which immediately surround the heat cells. Any remaining portions of the continuous layer or layers which surround the softened portions preferably remain more rigid. The narrow, softened portions act as hinges between the heat cells and between any remaining, cooler, more rigid portions, bending preferentially more than either the heat cells or more rigid portions. This results in thermal packs which possess sufficient rigidity to maintain structural support of the heat cells, to prevent unacceptable stretching of structures of the continuous layer or layers during processing or use, and to deter easy access to heat cell contents, while still maintaining good overall drape characteristics when heated. The thermal pack or packs, when incorporated into the disposable thermal body pads of the present invention, provide efficient and effective heat coverage by having excellent conformity with the user's body.

The present inventors have also discovered that it may be desirable to selectively place heat cells, in the thermal pack or packs when incorporated into the body pads of the present invention, into positions fixed within or to the unified structure of the thermal pack, relative to each other which are sufficiently close so as to block some or all possible axes, which otherwise would have passed uninterrupted between the heat cells, through the thermal pack, or select regions thereof, to minimize or eliminate undesirable, uninterrupted fold lines, and/or to increase the structural support that the heat cell matrix imparts to the thermal pack. That is, placement of the heat cells into positions relative to each other which are sufficiently close to block some or all possible axes which would otherwise have passed uninterrupted, between the heat cells, causes the thermal packs to fold along a multiplicity of short interconnected fold lines oriented in a number of different directions relative to each other. Folding along a multiplicity of interconnected fold lines results in good overall drape characteristics.

It is therefore an object of the present invention to provide disposable thermal body pads comprising one or more thermal packs having a unified structure of at least one continuous layer, preferably of a semirigid material which has different stiffness characteristics over a range of temperatures, and a plurality of individual heat cells, which provide a controlled and sustained temperature and which reach their operating temperature range relatively quickly. The heat cells are spaced apart and fixed within or to the unified structure of the thermal pack.

It is another object of the present invention to provide disposable thermal body pads having good overall drapability while maintaining sufficient rigidity to maintain structural support of the heat cells and prevent unacceptable stretching of the continuous layer or layers during processing or use.

It is also an object of the present invention to provide disposable thermal body pads which adapt to a wide variety of body contours providing consistent, convenient and comfortable heat application while deterring easy access to heat cell contents.

It is a further object of the present invention to provide disposable thermal body pads comprising a means for attaching the thermal body pad to a user's clothing so that the opposite side of the thermal body pad may be worn directly against the user's skin.

It is a still further object of the present invention to provide methods of treating acute, recurrent, and/or chronic pain, including skeletal, muscular, and/or referred pain, of a person suffering from such pain, by maintaining a sustained skin temperature of from about 32° C. to about 50° C. for a period of time of from about twenty seconds to about twenty-four hours, preferably by maintaining a skin temperature of from about 32° C. to about 43° C. for a time period of greater than about 1 hour to provide prolonged relief from such pain.

These objectives and additional objectives will become readily apparent from the detailed description which follows.

SUMMARY OF THE INVENTION

The disposable thermal body pads of the present invention comprise a substantially planar laminate structure having a first side, a second side, and one or more thermal packs comprising a unified structure having at least one continuous layer of a material, preferably which is semirigid at a temperature of about 25° C., having a tensile strength of about 0.7 g/mm$^2$ or greater, and at least two-dimensional drape, and which is substantially less rigid at a temperature of 35° C. or greater, having a tensile strength substantially less than the tensile strength of the material at about 25° C.

The continuous layer or layers of material of the present invention preferably comprise a coextruded material, more preferably a coextruded material comprising polypropylene, most preferably a coextruded material wherein a first side comprises polypropylene and a second side comprises a tie-layer of a low melt temperature copolymer, preferably EVA, preferably having a combined basis weight thickness of less than about 50 $\mu$m.

The thermal pack or packs further comprise a plurality of heat cells, preferably comprising an oxygen activated, heat generating chemistry comprising powdered iron, powdered activated charcoal, water, and salt, spaced apart and fixed within or to the unified structure of the thermal pack, which provide controlled and sustained temperature and which reach their operating temperature range quickly. Preferably the heat cells are placed into positions fixed within or to the unified structure of the thermal pack, relative to each other and sufficiently close so that some or all of the possible axes that would otherwise pass uninterrupted between the heat cells are blocked by the heat cells to cause the thermal packs to fold along a multiplicity of short interconnected fold lines.

The laminate structure further comprises means for providing oxygen permeability, preferably located on the first side of the laminate structure, to the plurality of heat cells, and means for releasably attaching the thermal body pad to an inside portion of a user's clothing, preferably located on the first side of the laminate structure, such that the second side of the thermal body pad may be placed directly against a user's body.

The present invention still further comprises methods of treating acute, recurrent, and/or chronic pain, including skeletal, muscular, and/or referred pain, of a person having such pain, by applying the disposable thermal body pads of the present invention to the afflicted body part of a person having such pain, to maintain a sustained skin temperature of from about 32° C. to about 50° C. for a period of time of from about twenty seconds to about twenty-four hours, preferably to maintain a skin temperature of from about 32° C. to about 43° C. for a time period of greater than about 1 hour, to provide prolonged relief from such pain.

All percentages and ratios used herein are by weight of the total composition, and all measurements made at 25° C., unless otherwise specified.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

Figure 1:
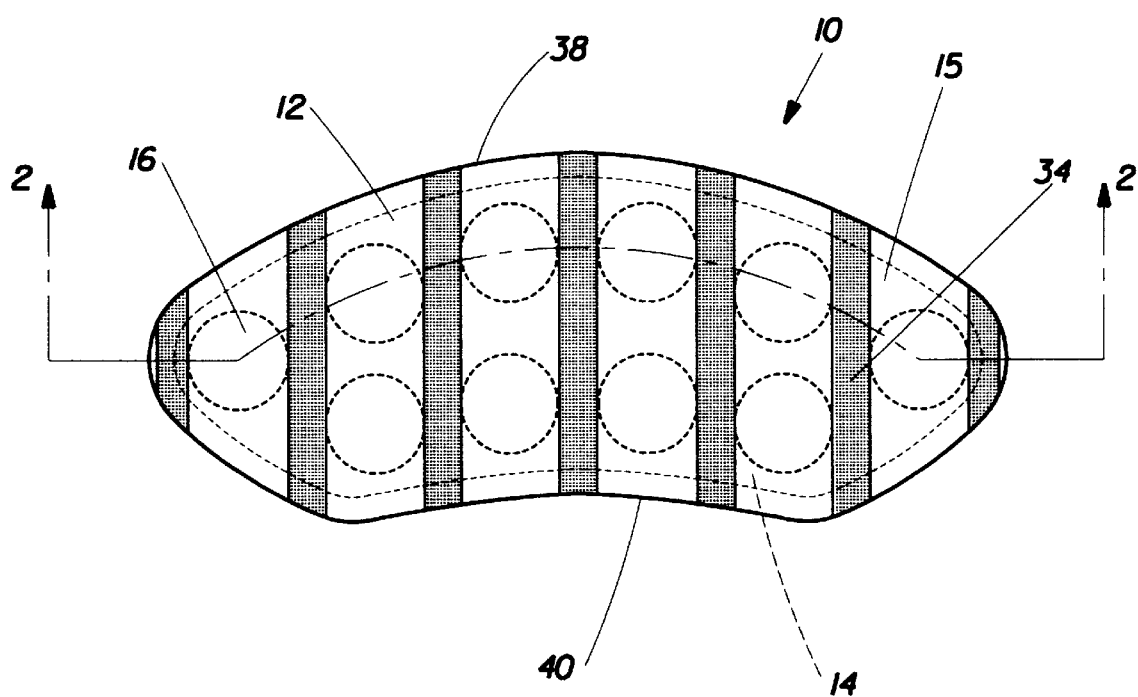
FIG. 1 is a plan view of a preferred embodiment of the disposable thermal body pad of the present invention, disclosing a pattern of heat cells and attachment adhesive stripes between the cells.

The disposable thermal body pads of the present invention comprise one or more thermal packs having at least one continuous layer of a material which preferably exhibits specific thermophysical properties and a plurality of individual heat cells, which preferably comprise an exothermic composition, spaced apart and fixed within or to the structure of the disposable thermal pack.

The material of the at least one continuous layer is preferably semirigid when at room temperature, i.e., about 25° C., or below, but softens and becomes substantially less rigid when heated to about 35° C., or greater. Therefore, when heat cells, which are fixed within or to the unified structure of the thermal packs, are active, that is at a heat cell temperature of about 35° C. or greater, the narrow portion of the continuous layer or layers of material immediately surrounding each heat cell preferably softens and acts as a hinge between the heat cells and between any remaining, more rigid portions of the continuous layer or layers, bending preferentially more than either the heat cells or any cooler, more rigid portions. This results in thermal packs which possess sufficient rigidity to maintain structural support of the heat cells and prevent unacceptable stretching of structures of the continuous layer or layers during processing or use, while still maintaining good overall drape characteristics when heated. The disposable thermal body pads of the present invention provide consistent, convenient, and comfortable heat application, and an excellent conformity with user's body, while retaining sufficient rigidity to deter easy access to heat cell contents.

"Disposable", as used herein, means that, while the thermal body pads of the present invention may be stored in a resealable, substantially air-impermeable container and reapplied to the user's body as often as required for the relief of pain, they are intended to be thrown away, i. e., deposited in a suitable trash receptacle, after the heat source, i. e., the heat cell(s) or thermal pack(s), has been fully expended.

"Heat cells", as used herein, means a unified structure, comprising an exothermic composition, preferably a specific iron oxidation chemistry, enclosed within two layers, wherein at least one layer may be oxygen permeable, capable of providing long lasting heat generation with improved temperature control, and having specific physical dimensions and fill characteristics. These heat cells can be used as individual heating units, or in a thermal pack comprising a plurality of individual heat cells which can also be easily incorporated into disposable body wraps, pads, and the like. Thermal packs and body wraps incorporating thermal packs adapt to a wide variety of body contours, thus providing consistent, convenient, and comfortable heat application.

"Plurality of heat cells", as used herein, means more than one, preferably more than two, more preferably more than three, most preferably more than four, heat cells.

"Agglomerated pre-compaction composition", as used herein, means the mixture of dry powdered ingredients, comprising iron powder, carbonaceous powder, metal salt (s), water-holding agent(s), agglomeration aid(s), and dry binder(s) prior to direct compaction.

"Direct compaction", as used herein, means a dry powder mixture is blended, compressed, and formed into pellets, tablets, or slugs without the use of typical wet binders/solutions to adhere the particulate(s) together. Alternatively, the dry powder mixture is blended and roll compacted or slugged, followed by milling and screening, creating directly compacted granules. Direct compaction may also be known as dry compaction.

"Heating element(s)", as used herein, means the exothermic, direct compacted, dry agglomerated pre-compaction composition formed into compaction articles, such as granules, pellets, slugs, and/or tablets capable of generating heat, after an aqueous solution such as water or brine (salt solution) is added, by the exothermic oxidation reaction of iron. Agglomeration granules of said agglomerated pre-compaction composition are also included as heating elements herein.

The "fill volume", as used herein, means the volume of the particulate composition or the compacted, water-swelled, heating element in the filled heat cell. The "void volume", as used herein, means the volume of the cell left unfilled by the particulate composition or the compacted, water-swelled, heating element in a finished heat cell, not including the unfilled space within a tablet comprising a hole or reservoir, in a finished heat cell, measured without differential pressure in the heat cell and without additional stretching or deformation of the substrate material. The "cell volume", as used herein, means the fill volume plus the void volume of the heat cell.

"Continuous layer or layers", as used herein, means one or more layers of a material which may be uninterrupted or partially, but not completely, interrupted by another material, holes, perforations, and the like, across its length and/or width.

"Rigid", as used herein, means the property of a material wherein the material may be flexible, yet is substantially stiff and unyielding, and which does not form fold lines in response to gravitational pull or other modest forces.

"Semirigid material", as used herein, means a material which is rigid to some degree or in some parts, i. e., having at least two-dimensional drape at a temperature of about 25° C., and exhibits a toughness to maintain structural support of the heat cells in an unsupported format, and/or prevent unacceptable stretching of structures of the material during processing or use, while still maintaining good overall drape characteristics when heated, and/or retaining sufficient rigidity to deter easy access to deter easy access to heat cell contents.

"Two dimensional drape", as used herein, means drape which occurs across a continuous layer or layers, across a thermal pack, or across a select region of a layer or layers, or thermal pack, exclusively along one axis, i.e., one fold line forms, at the expense of other axes in response to gravitational pull or other modest forces.

"Three dimensional drape", as used herein, means drape which simultaneously occurs across a continuous layer or layers, across a thermal pack, or across a select region of a layer or layers, or thermal pack, along two or more axes, i. e., two or more fold lines form, in response to gravitational pull or other modest forces.

"Fold lines", as used herein, means the line along which a material forms a temporary or permanent crease, ridge, or crest in response to gravitational pull or other modest forces.

It is understood that the disposable thermal body pads of the present invention may comprise one or more thermal packs. However, for clarity a disposable thermal body pad comprising a single thermal pack will be described herein.

Figure 2:
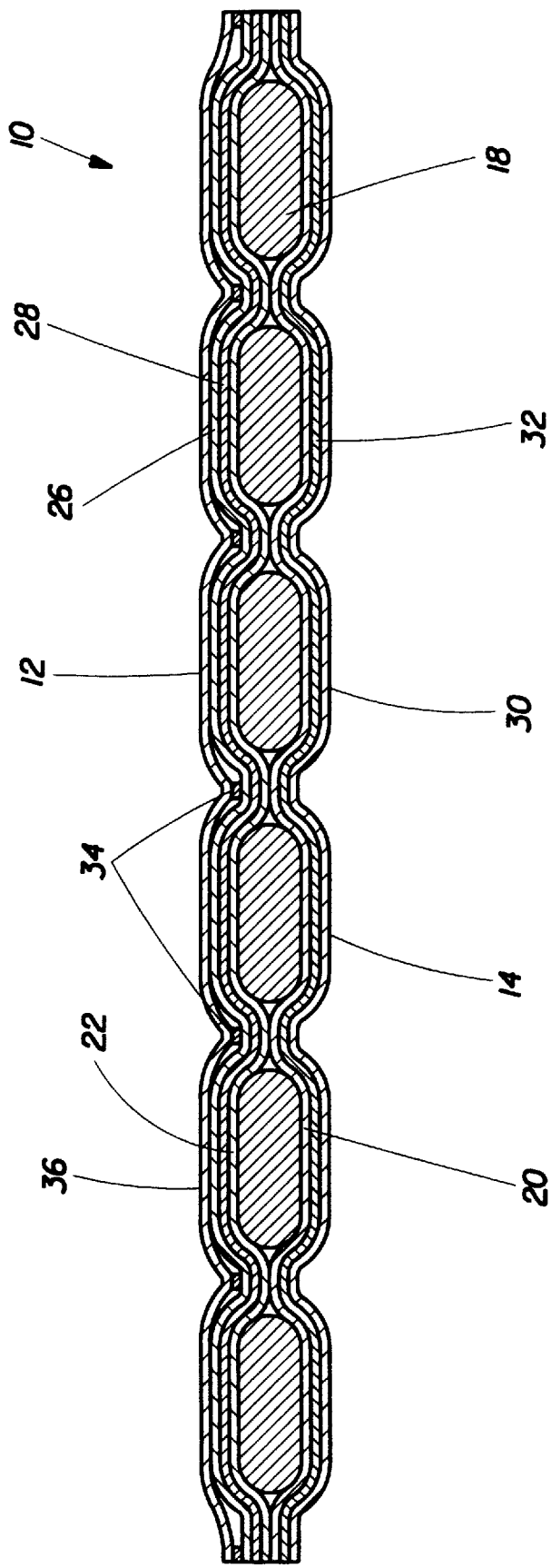
FIG. 2 is sectioned side elevation of FIG. 1.

Referring now to the drawings, and more particularly to FIGS. 1 and 2, there is shown a preferred embodiment of the present invention, which provides a thermal body pad, generally indicated as 10, preferably having a substantially planar laminate structure, and one or more thermal packs 15. The laminate structure comprises a first side 12, having attachment and oxygen permeability means, which is positioned away from the body during wear, and a second side 14 which is positioned against the body during wear.

Each thermal pack 15 comprises a plurality of individual heat cells 16, preferably fixed within or to the unified structure of the thermal pack 15. While it is preferred that heat cells 16 are embedded within the laminate structure of thermal pack 15, each thermal pack 15 may alternatively comprise a single continuous base layer 20, wherein individual, or groups of heat cells 16 are fixedly attached and spaced apart across the base layer 20. These heat cells 16 are spaced apart from each other and each heat cell 16 functions independently of the rest of the heat cells 16. Each heat cell 16 preferably comprises a densely packed, particulate exothermic composition 18 which substantially fills the available cell volume within the cell reducing any excess void volume thereby minimizing the ability of the particulate matter to shift within the cell. Alternatively, the exothermic composition 18 may be compressed into a hard tablet before being placed in each cell. Because the heat generating material is densely packed or compressed into a tablet, the heat cells 16 are not readily flexible. Therefore, the spacing apart of the cells and the materials selected for cell forming base layer 20 and cell covering layer 22 between the heat cells 16 allows each thermal pack 15 to easily conform to the user's body more readily than a single large cell.

Continuous cell forming base layer 20 and cell covering layer 22 may be made of any number of suitable materials. Preferably cell forming base layer 20 and cell covering layer 22 comprises materials which are semirigid at a temperature of about 25° C. and which soften, i.e., become substantially less rigid, at a temperature of about 35° C., or greater. That is, the materials preferably have a tensile strength, within the elastic deformation range of the material, of about 0.7 g/mm$^2$ or greater, more preferably about 0.9 g/mm$^2$ or greater, most preferably about 1 g/mm$^2$ or greater, at about 25° C. and a tensile strength substantially less at about 35° C. or greater. "Substantially less", as used herein, means that the tensile strength of the material at about 35° C., or greater, is statistically significantly less than the tensile strength at about 25° C., at an appropriate statistical confidence (i. e., 95%) and power (i. e., $\geq 90\%$).

Therefore, when heat cells 16, which are fixed within or to the unified structure of thermal pack 15, are active, that is at a heat cell temperature of from about 35° C. to about 60° C., preferably from about 35° C. to about 50° C., more preferably from about 35° C. to about 45° C., and most preferably from about 35° C. to about 40° C., the narrow portion of the continuous layer or layers of material immediately surrounding each heat cell softens and acts as a hinge between the heat cells and between any remaining, cooler, more rigid portions of the continuous layer or layers, bending preferentially more than either the heat cell or more rigid portions. This results in thermal packs 15 which possess sufficient rigidity to maintain structural support of the heat cells and to prevent unacceptable stretching of structures of the continuous layer or layers during processing or use, while still maintaining good overall drape characteristics when heated.

When thermal pack 15 of the present invention is incorporated into body pad 10, body pad 10 easily adapts to a wide variety of body contours, provides consistent, convenient, and comfortable heat application, and an excellent conformity with body forms, while retaining sufficient rigidity to prevent pad 10 from folding or bunching during use and deter easy access to heat cell contents.

Typically, the tensile strength is measured using a simple tensile test on an electronic tensile test apparatus, such as a universal constant rate elongation tensile testing machine with computer, Instron Engineering Corp., Canton, Mass. Any standard tensile test may be used, for example, material samples are cut into strips having a width of about 2.54 cm (about 1 inch) and a length of from about 7.5 cm to about 10 cm (about 3 to about 4 inches). The ends of the strips are placed into the jaws of the apparatus with enough tension to eliminate any slack, but without loading the load cell. The temperature of the sample is then allowed to stabilize at the desired test temperature. The load cell of the apparatus is set for about 22.7 kg (50 pound) load, the elongation set for 5 mm, and the crosshead speed is set for about 50 cm/min. The apparatus is started and the tensile strength data is collected by the computer. The sample is then removed from the apparatus.

The tensile strength may be calculated as the slope of the tensile load vs. the extension during elastic deformation of the materials using the equation:

$$m = (L/E)$$

Where m=the slope in g/mm$^2$ during elastic deformation;
L=the load at extension in g/mm; and
E=the extension in mm.

Cell forming base layer 20 and/or cell covering layer 22 also preferably comprise at least two-dimensional drape at about 25° C., i. e., a single fold or crease occurs in the material along a single axis, and preferably three-dimensional drape at about 35° C. or greater, i. e., two or more folds or creases occur along multiple axes. Drape may be determined by placing and centering a square sample, for example about 30 cm by about 30 cm (about 12 inches by about 12 inches), of material on the end of a cylindrical shaft with a pointed end, allowing the material to drape due to gravitational forces, and the number of fold lines counted. Materials that exhibit one-dimensional drape, i. e., have no folds or creases in any direction, are determined to be rigid, while materials that at least two-dimensional drape, i. e., have at least one fold or crease line forming along at least one axis, are determined to be semirigid.

Different materials may be capable of satisfying the specified requirement for continuous cell forming base layer and/or cell covering layer 20 and/or 22 provided that the thickness is adjusted accordingly. Such materials may include, but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof. These materials may be used alone, preferably extruded, more preferably coextruded, most preferably coextruded with a low melt temperature polymer including, but not limited to, ethylene vinyl acetate copolymer, low density polyethylene, and mixtures thereof.

Cell forming base layer 20 and/or cell covering layer 22 preferably comprise polypropylene, more preferably a coextruded material comprising polypropylene, most preferably a coextruded material wherein a first side comprises polypropylene, preferably from about 10% to about 90%, more preferably from about 40% to about 60%, of the total thickness of the material, and a second side comprises a tie-layer of a low melt temperature copolymer, preferably EVA. Cell forming base layer 20 and/or cell covering layer 22 preferably have a basis weight thickness of less than about 50 μm, more preferably less than about 40 μm, most preferably less than about 30 μm.

Cell forming base layer 20 and/or cell covering layer 22 preferably comprise a coextruded material, having a first side of polypropylene and a second side of EVA, and having a combined thickness of from about 2 μm to about 30 μm, preferably about 25 μm (1 mil), wherein the polypropylene comprises about 50% and the EVA tie-layer comprises about 50% of the total thickness of cell forming base layer 20 and/or cell covering layer 22. A particularly preferred material is available as P18-3161 from Clopay Plastics Products, Cincinnati, Ohio. The P18-3161 which is preferred for cell covering layer 22 has been subjected to a post process aperturing with hot needles to render it permeable to oxygen.

When coextruded materials of the type just described are used for cell forming base layer 20 and cell covering layer 22, the EVA sides are preferably oriented toward each other to facilitate thermal bonding of cell covering layer 22 to cell forming base layer 20.

Good overall drape characteristics and/or excellent conformity with user's body, and/or increased structural support to the thermal pack 15, may also be achieved by selectively placing the heat cells 16 into positions fixed within or to the unified structure of the thermal pack 15 relative to each other which are sufficiently close so as to block some or all possible axes across the material of the continuous layer and/or layers 20 and/or 22, which otherwise would have passed uninterrupted between the heat cells 16, through the thermal pack 15, or select regions thereof, to minimize or eliminate undesirable, uninterrupted fold lines. That is, placement of the heat cells 16 into positions relative to each other which are sufficiently close so that the number of axes which pass uninterrupted, between the heat cells 16, is selectively controlled, such that the continuous cell forming base layer 20 and cell covering layer 22 of thermal pack 15, or select regions thereof, preferably folds along a multiplicity of short interconnected fold lines oriented in a number of different directions relative to each other. Folding along a multiplicity of interconnected fold lines results in thermal packs 15 which have good overall drape characteristics, readily conform with user's back, and/or have increased structural support of the heat cell matrix.

Because heat cells 16 are not readily flexible, the spacing between heat cells 16 provides the preferred benefits and may be determined, when selectively placing heat cells 16 within or fixed to the unified structure of thermal packs 15, wherein at least one heat cell of four adjacent heat cells, whose centers form a quadrilateral pattern, blocks one or more axes that could otherwise form at least one fold line tangential to the edges of one or more pairings of the remaining three heat cells in the quadrilateral pattern. Preferably, the spacing between the at least one heat cell of the four adjacent heat cells and each of the heat cells of the one or more pairings of the remaining heat cells in the quadrilateral pattern may be calculated using the equation:

$$s \leq (W_q/2)*0.75$$

Where s=the closest distance between the heat cells; and
$W_q$=the measurement of the smallest diameter of the smallest diameter heat cell within the quadrilateral pattern.

Alternatively, the spacing between heat cells 16 may be determined wherein, at least one heat cell of three adjacent heat cells, whose centers form a triangular pattern, blocks one or more axes that could otherwise form at least one fold line tangential to the edges of the remaining pair of heat cells in the triangular pattern formed by the three heat cells. Most preferably, the spacing between the at least one heat cell of the three adjacent heat cells and each heat cell of the remaining pair of heat cells in the triangular pattern may be calculated using the equation:

$$s \leq (W_t/2)*0.3$$

Where s=the closest distance between the heat cells; and
$W_t$=the measurement of the smallest diameter of the smallest diameter heat cell within the triangular pattern.

Different materials may be capable of satisfying the above specified requirements. Such materials may include, but are not limited to, those materials mentioned above.

A most preferred embodiment of the disposable thermal packs 15 of the present invention comprises at least one continuous layer of semirigid material having the thermophysical properties described above, and the heat cells 16 fixed within or to the unified structure of thermal pack 15 in positions relative to each other which are sufficiently close so as to block some or all possible axes across the material of the continuous layer(s) 20 and/or 22, which otherwise would have passed uninterrupted between heat cells 16, through thermal packs 15, or select regions thereof, to minimize or eliminate undesirable, uninterrupted fold lines, as described above.

Exothermic composition 18 may comprise any composition capable of providing heat. However, exothermic composition 18 preferably comprises a particulate mix of chemical compounds that undergo an oxidation reaction during use. Alternatively, exothermic composition 18 may also be formed into agglomerated granules, direct compacted into compaction articles such as granules, pellets, tablets, and/or slugs, and mixtures thereof. The mix of compounds typically comprises iron powder, carbon, a metal salt(s), and water. Mixtures of this type, which react when exposed to oxygen, providing heat for several hours.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air. Typically, the iron powder comprises from about 30% to about 80% by weight, preferably from about 50% to about 70% by weight, of the particulate exothermic composition.

Active carbon prepared from coconut shell, wood, charcoal, coal, bone coal, etc. are useful, but those prepared from other raw materials such as animal products, natural gas, fats, oils and resins are also useful in the particulate exothermic composition of the present invention. There is no limitation to the kinds of active carbon used, however, the preferred active carbon has superior water holding capabilities and the different carbons may be blended to reduce cost. Therefore, mixtures of the above carbons are useful in the present invention as well. Typically, activated carbon, non-activated carbon, and mixtures thereof, comprises from about 3% to about 25%, preferably from about 8% to about 20%, most preferably from about 9% to about 15% by weight, of the particulate exothermic composition.

The metal salts useful in the particulate exothermic composition include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. In general, several suitable alkali, alkaline earth, and transition metal salts exist which can also be used, alone or in combination, to sustain the corrosive reaction of iron. The preferred metal salts are sodium chloride, cupric chloride, and mixtures thereof. Typically, the metal salt(s) comprises from about 0.5% to about 10% by weight, preferably from about 1.0% to about 5% by weight, of the particulate exothermic composition.

The water used in the particulate exothermic composition may be from any appropriate source. There is no particular limitation to its purity, kind, etc. Typically, water comprises from about 1% to about 40% by weight, preferably from about 10% to about 30% by weight, of the particulate exothermic composition.

Additional water-holding materials may also be added as appropriate. Useful additional water-holding materials include vermiculite, porous silicates, wood powder, wood flour, cotton cloth having a large amount of fluffs, short fibers of cotton, paper scrap, vegetable matter, super absorbent water-swellable or water-soluble polymers and resins, carboxymethylcellulose salts, and other porous materials having a large capillary function and hydrophilic property can be used. Typically, the additional water-holding materials comprise from about 0.1% to about 30% by weight, preferably from about 0.5% to about 20% by weight, most preferably from about 1% to about 10% by weight, of the particulate exothermic composition.

Other additional components include agglomeration aids such as gelatin, natural gums, cellulose derivatives, cellulose ethers and their derivatives, starch, modified starches, polyvinyl alcohols, polyvinylpyrrolidone, sodium alginates, polyols, glycols, corn syrup, sucrose syrup, sorbitol syrup and other polysaccharides and their derivatives, polyacrylamides, polyvinyloxoazolidone, and maltitol syrup; dry binders such as maltodextrin, sprayed lactose, co-crystallized sucrose and dextrin, modified dextrose, sorbitol, mannitol, microcrystalline cellulose, microfine cellulose, pre-gelatinized starch, dicalcium phosphate, and calcium carbonate; oxidation reaction enhancers such as elemental chromium, manganese, or copper, compounds comprising said elements, or mixtures thereof; hydrogen gas inhibitors such as inorganic or organic alkali compounds or alkali weak acid salts including sodium hydroxide, potassium hydroxide, sodium hydrogen carbonate, sodium carbonate, calcium hydroxide, calcium carbonate, and sodium propionate; fillers such as natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents such as tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. The preferred surfactant, if used however, is nonionic. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 $\mu$m, preferably less than 150 $\mu$m.

The above-mentioned components of the composition are blended using conventional blending techniques. Suitable methods of blending these components are described in detail in U.S. Pat. No. 4,649,895 to Yasuki et al., issued Mar. 17, 1987 which is incorporated by reference herein in its entirety.

Alternatively to the above described particulate exothermic composition, the exothermic composition may be formed into agglomerated granules, direct compacted into compaction articles such as granules, pellets, tablets, and/or slugs, and mixtures thereof.

The exothermic composition of these agglomerated granules and/or compaction articles comprises iron powder, dry powdered carbonaceous material, an agglomeration aid, and a dry binder. Additionally, a metal salt, is added to the dry mix or subsequently as an aqueous/brine solution. Typically, the iron powder comprises from about 30% to about 80%, preferably from about 40% to about 70%, most preferably from about 50% to about 65% by weight; activated carbon, non-activated carbon, and mixtures thereof, comprises from about 3% to about 20%, preferably from about 5% to about 15%, most preferably from about 6% to about 12% by weight; the metal salt(s) comprises from about 0.5% to about 10%, preferably from about 1% to about 8%, most preferably from about 2% to about 6% by weight; the agglomeration aids comprise from about 0% to about 9%, preferably from about 0.5% to about 8%, more preferably from about 0.6% to about 6%, most preferably from about 0.7% to about 3% by weight; and the dry binder comprises from about 0% to about 35%, preferably from about 4% to about 30%, more preferably from about 7% to about 20%, most preferably from about 9% to about 15% by weight, of the agglomerated pre-compaction compositions of the present invention.

Heat cells comprising agglomerated granules are typically made using conventional blending techniques and agglomerated into granules.

Heat cells comprising compaction articles are preferably made by direct compaction of the dry ingredients into articles such as hard granules, pellets, tablets, and/or slugs. Suitable methods of making tablets and/or slugs are described in detail in Chapter 89, "Oral Solid Dosage Forms", *Remington's Pharmaceutical Sciences*, $18^{th}$ Edition, (1990), pp. 1634–1656, Alfonso R. Gennaro, ed., incorporated herein by reference in its entirety. Any conventional tableting machine and compression pressures, up to the maximum provided by the machine can be used.

The tablets/slugs can have any geometric shape consistent with the shape of the heat cell, e.g., disk, triangle, square, cube, rectangle, cylinder, ellipsoid and the like, all or none of which may contain a hole through the middle or other reservoir. The preferred shape of the tablet/slug comprises a disk shaped geometry, having a concaved (whisper) configuration to the top and/or bottom of the tablet. The more preferred shape of the tablet/slug, however, comprises a disk shaped geometry, having a hole perpendicular to, and through the middle of the top and bottom of the tablet.

The size of the compacted disk is limited only by the size of the punches and die available and/or used in the tableting machine, as well as the size of the heat cell pocket. However, the disk typically has a diameter of from about 0.2 cm to about 10 cm, preferably from about 0.5 cm to about 8 cm, more preferably from about 1 cm to about 5 cm, and most preferably from about 1.5 cm to about 3 cm and a height of from about 0.08 cm to about 1 cm, preferably from about 0.15 cm to about 0.8 cm, more preferably from about 0.2 cm to about 0.6 cm, and most preferably from about 0.2 cm to about 0.5 cm. Alternatively, the compacted disk having a geometric shape other than a disk shape may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from about 0.08 cm to about 1 cm, preferably from about 0.15 cm to about 0.8 cm, more preferably from about 0.2 cm to about 0.6 cm, and most preferably from about 0.2 cm to about 0.5 cm, and a length at its longest point of from about 1.5 cm to about 20 cm, preferably from about 1 cm to about 15 cm, more preferably from about 1 cm to about 10 cm, most preferably from about 3 cm to about 5 cm. The hole or reservoir should be large enough to substantially hold the prescribed amount of water and/or the water-carrying material. Typically, the hole has a diameter of from about 0.1 cm to about 1 cm, preferably from about 0.2 cm to about 0.8 cm, and more preferably from about 0.2 cm to about 0.5 cm.

The compaction articles of the present invention are compressed to the hardest possible mechanical strength to withstand the shocks of handling in their manufacture, packing, shipping, and dispensing. The compaction articles are typically compressed to a density of greater than about 1 g/cm$^3$, preferably from about 1 g/cm$^3$ to about 3 g/cm$^3$, more preferably from about 1.5 g/cm$^3$ to about 3 g/cm$^3$, and most preferably from about 2 g/cm$^3$ to about 3 g/cm$^3$.

Heat cells 16 comprising the above described components are typically formed by adding a fixed amount of a particulate exothermic composition or compaction article(s) 18 to a pocket or pockets made in a first continuous layer, i. e., cell forming layer 20. A second continuous layer, i. e., cell covering layer 22, is placed over the first continuous layer, sandwiching the particulate exothermic composition or compaction article(s) between the two continuous layers which are then bonded together, preferably using a low heat, forming a unified, laminate structure. Preferably, each heat cell has a similar volume of heat generating material and has similar oxygen permeability means. However, the volume of the heat generating material, shape of the heat cell, and oxygen permeability may be different from heat cell to heat cell as long as the resulting cell temperatures generated are within accepted therapeutic and safety ranges for their intended use.

The heat cells 16 of thermal pack 15 can have any geometric shape, e.g., disk, triangle, pyramid, cone, sphere, square, cube, rectangle, rectangular parallelepiped, cylinder, ellipsoid and the like. The preferred shape of the heat cells 16 comprises a disk shaped geometry having a cell diameter of from about 0.2 cm to about 10 cm, preferably from about 0.5 cm to about 8 cm, more preferably from about 1 cm to about 5 cm, and most preferably from about 1.5 cm to about 3 cm. The heat cells 16 have a height of from greater than about 0.2 cm to about 1 cm, preferably from greater than about 0.2 cm to about 0.9 cm, more preferably from greater than about 0.2 cm to about 0.8 cm, and most preferably from greater than about 0.3 cm to about 0.7 cm. Alternatively, the heat cells having geometric shapes other than a disk shape, preferably an ellipsoid (i. e., oval), may have a width at its widest point of from about 0.15 cm to about 20 cm, preferably from about 0.3 cm to about 10 cm, more preferably from about 0.5 cm to about 5 cm, most preferably from about 1 cm to about 3 cm, a height at its highest point of from greater than about 0.2 cm to about 5 cm, preferably from greater than about 0.2 cm to about 1 cm, more preferably from greater than about 0.2 cm to about 0.8 cm, and most preferably from about 0.3 cm to about 0.7 and a length at its longest point of from about 0.5 cm to about 20 cm, preferably from about 1 cm to about 15 cm, more preferably from about 1 cm to about 10 cm, most preferably from about 3 cm to about 5 cm.

The ratio of fill volume to cell volume of the heat cells 16 is from about 0.7 to about 1.0, preferably from about 0.75 to about 1.0, more preferably from about 0.8 to about 1.0, even more preferably from about 0.85 to about 1.0, and most preferably from about 0.9 to about 1.0.

Oxygen permeability in cell covering layer 22 is preferably a plurality of apertures in cell covering layer 22, which are made by piercing cell covering layer 22 with hot needles. The size of the apertures is preferably about 0.127 mm diameter, and there are preferably 25 to 40 apertures per heat generating cell. Another preferred method of making apertures is to pierce cell covering layer 22 with cold needles. Alternatively, apertures may be produced by a vacuum forming or a high pressure water jet forming process. Yet another method is making cell covering layer 22 from a microporous membrane or a semi-permeable membrane. Such membrane may be combined with a highly porous carrier material to facilitate processing. The oxygen permeability required ranges from about 0.01 cc $O_2$ per minute per 5 square cm to about 15 cc $O_2$ per minute per 5 square cm at 21° C. and 1 ATM.

The velocity, duration, and temperature of the thermogenic oxidation reaction of the exothermic composition 18 can be controlled as desired by changing the area of contact with air, more specifically, by changing the oxygen diffusion/permeability.

Preferably, each heat cell 16 has a similar volume of chemistry and has a similar oxygen permeability means. Alternatively, chemistry volumes, shapes, and oxygen permeability means can be different from cell to cell as long as the resulting cell temperatures generated are similar.

On either side of heat cells 16 of thermal pack 15 are additional layers of material. On first side 12 is a first outer fabric 26 attached to cell covering layer 22 by a first adhesive layer 28. First outer fabric 26 and first adhesive layer 28 are preferably more permeable to air than is cell covering layer 22. Furthermore, first outer fabric 26 and first adhesive layer 28 preferably do not appreciably alter the oxygen permeability of cell covering layer 22. Therefore, cell covering layer 22 alone controls the flow rate of oxygen into each heat generating cell 16.

On second side 14 of thermal body pad 10 is a second outer fabric 30, which is attached to cell forming base layer 20 by a second adhesive layer 32. Preferably, first outer fabric 26 and second outer fabric 30 are made of similar materials, and first adhesive layer 28 and second adhesive layer 32 are made of the same materials.

Preferably, first side 12 of thermal body pad 10 has an attachment means 34 for releasably attaching thermal body pad 10 to clothing. Attachment means 34 may be an adhesive. If an adhesive, then attachment means 34 may have a release paper 36 attached to the adhesive in order to protect adhesive 34 from prematurely sticking to a target other than the intended user's clothing. Attachment means 34 preferably has a stronger bond to first outer fabric 26 than to either release paper 36 or to any target surface. In the alternative, attachment means 34 for releasably attaching thermal body pad 10 to clothing may be located on second side 14.

Alternatively, attachment means 34 may be an adhesive coated film attached to first outer fabric 26. If the adhesive coated film has standoffs to prevent adhesion until the target surface and the film are pressed together to expose the adhesive, then release paper 36 may be eliminated. Attachment means 34 may also comprise mechanical fasteners attached to first outer fabric 26, which provide sufficient engagement with different varieties of clothing to enable fixed positioning to be achieved. If mechanical fasteners are used, release paper 36 may also be eliminated.

Thermal body pad 10 has an upper edge 38 and a lower edge 40 opposite the pad from upper edge 38. These edges are so designated because of the orientation of the pad when it is preferably used as a menstrual pain heating pad and placed inside a woman's clothing, i. e., panties, to rest against her abdomen. Attachment means 34 are used to attach thermal body pad 10 to inner surface of clothing after release paper 36 has been removed.

Attachment means 34, for releasably attaching thermal body pad 10 to clothing, may be any number of suitable adhesives and application patterns. A preferred adhesive is Dispomelt™ 34-5598 pressure sensitive hot melt adhesive available from National Starch and Chemical Company of Bridgewater, N.J. This adhesive may be applied to first outer fabric 26 by slot die coating or printing. In either case it is desirable that the adhesive penetrate into first outer fabric 26 so that the adhesive preferentially sticks to first outer fabric 26 upon removal of thermal body pad 10 from the user's clothing after use. The preferred pattern of adhesive produced by this method is straight parallel stripes extending from upper edge 38 to the lower edge 40 of thermal body pad 10, and located between heat cells 16, as depicted in FIG. 1, however, other patterns may also be used as appropriate. The relatively heavy adhesive stripes are oxygen impermeable. By positioning the stripes of adhesive between heat cells 16, oxygen permeability of cell covering layer 22 remains unhindered in its ability to pass oxygen to heat cells 16. Release paper 36 is preferably a silicone treated paper, such as BL 25 MGA SILOX C3R/0 release paper from Akrosil, Menasha, Wis.

In a particularly preferred embodiment of the present invention, first outer fabric 26 is preferably a soft flexible material. Materials suitable as first outer fabric 26 include, but are not limited to, formed films; fabrics including wovens, knits, and nonwovens, which are carded, spunbonded, air laid, thermally bonded, wet laid, meltblown, and/or through-air bonded. The material composition of first outer fabric 26 may be cotton, polyester, polyethylene, polypropylene, nylon, etc. A particularly suitable material for first outer fabric is 32 grams per square meter (gsm), hydrophobic, polypropylene, carded thermal bonded fabric available as grade #9327786 from Veratec, Walpole, Mass.

Preferably, second outer fabric 30 is a soft, flexible, non-irritating-to-the-skin material. Materials suitable as second outer fabric 30 include but are not limited to: formed films; fabrics including wovens, knits, and nonwovens, which are carded, spunbonded, air laid, thermally bonded, wet laid, meltblown, and/or through-air bonded. The material of second outer fabric 30 may be cotton, polyester, polyethylene, polypropylene, nylon, etc. A particularly suitable material for second outer fabric 30 is 65 gsm polypropylene carded thermally bonded fabric available as grade #9354790 from Veratec, Walpole, Mass.

Adhesive layer 28 is applied in such a manner that it does not interfere with oxygen permeability to heat cells 16. A suitable material and application method that has been successfully used for adhesive layers 28 and 32 are 70-4589 pressure sensitive hot melt adhesive available from National Starch and Chemical Co., Bridgewater, N.J, which is applied with spiral glue application system available from Nordson, Waycross, Ga.

Prior to use, thermal body pad 10 is typically enclosed within an oxygen impermeable package. Thermal body pad 10 is preferably folded in half with second side 14 internal to the fold and external side 12 exposed to the inside of the package. Thermal body pad 10 is removed from the oxygen impermeable package allowing oxygen to react with chemistry 18. This chemical oxidation system is compact and portable. Once the chemical reaction is completed, the thermal body pad is no longer capable of generating heat and it is intended to be appropriately discarded in the solid waste system.

By placing the attachment means on the same side as the oxygen permeable layer, the thermal body pad of the present invention may be worn inside a user's clothing and directly in contact with the user's body. Such direct contact by heat cells in the thermal body pad provides a known thermal resistance between heat generating chemistry and body surface. Thus, the chemistry can be designed to oxidize at a particular rate to produce a specified temperature.

The present invention further comprises a method for treating acute, recurrent, and/or chronic body pain, including muscular, skeletal, and/or referred body pain, of a person suffering such pain by topically applying heat to the specific areas of the body of a person suffering such pain. The method comprises maintaining a skin temperature to the specific areas of the body of a person suffering such pain of from about 32° C. to about 50° C., preferably from about 32° C. to about 45° C., more preferably from about 32° C. to about 42° C., most preferably from about 32° C. to about 39° C., still most preferably from about 32° C. to about 37° C., preferably by applying the above described body pads to the afflicted body part, preferably the abdominal or menstrual area, of a person suffering such pain, for from about twenty seconds to about twenty-four hours, preferably from about twenty minutes to about twenty hours, more preferably from about four hours to about sixteen hours, most preferably from about eight hours to about twelve hours, wherein the maximum skin temperature and the length of time of maintaining the skin temperature at the maximum skin temperature may be appropriately selected by a person needing such treatment, such that the desired therapeutic benefits are achieved, without any adverse events, such as skin burns which may be incurred by using a high temperature for a long period of time.

Preferably the method comprises maintaining a sustained skin temperature to the body of a person having acute, recurrent, and/or chronic body pain, including muscular, skeletal, and/or referred body pain, of from about 32° C. to about 43° C., preferably from about 32° C. to about 42° C., more preferably from about 32° C. to about 41° C., most preferably from about 32° C. to about 39° C., still most preferably from about 32° C. to about 37° C., for a time period of greater than about 1 hour, preferably greater than about 4 hours, more preferably greater than about 8 hours, even more preferably greater than about 16 hours, most preferably about 24 hours, to substantially relieve acute, recurrent, and/or chronic body pain, including skeletal, muscular, and/or referred body pain, such as abdominal and/or menstrual pain, of a person having such pain and to substantially prolong relief, for at least about 2 hours, preferably for at least about 8 hours, more preferably for at least about 16 hours, most preferably for at least about one day, still most preferably for at least about three days, from such pain, even after the heat source is removed from the afflicted body part of the user.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A disposable thermal body pad comprising:
a) at least one piece of flexible material having a first side, a second side, an upper edge, a lower edge, and one or more thermal packs, said thermal packs having a unified structure comprising at least one continuous layer of a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C., and a plurality of individual heat cells spaced apart and fixed within or to said unified structure of said thermal packs; and b) a means for releasably attaching said thermal body pad to an inside portion of user's clothing.

2. A disposable thermal body pad according to claim 1 wherein said at least one continuous layer comprises a tensile strength of about 0.85 g/mm$^2$, or greater, and at least two-dimensional drape at a temperature of about 25° C.

3. A disposable thermal body pad according to claim 2 wherein said at least one continuous layer comprises a tensile strength of about 1 g/mm$^2$, or greater, and at least two-dimensional drape at a temperature of about 25° C.

4. A disposable thermal body pad according to claim 1 wherein said at least one continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

5. A disposable thermal body pad according to claim 4 wherein said continuous layer comprises a coextruded material selected from the group consisting of polyethylene, polypropylene, nylon, polyester, polyvinyl chloride, polyvinylidene chloride, polyurethane, polystyrene, saponified ethylene-vinyl acetate copolymer and ethylene-vinyl acetate copolymer.

6. A disposable thermal body pad according to claim 5 wherein said at least one continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

7. A disposable thermal body pad according to claim 6 wherein said at least one continuous layer comprises a coextruded material having a first side of polypropylene and a second side of ethylene-vinyl acetate copolymer.

8. A disposable thermal body pad according to claim 7 wherein said at least one continuous layer comprises a coextruded film having a first side of polypropylene and a second side of ethylene vinyl acetate copolymer, wherein said polypropylene comprises from about 10% to about 90% of the total thickness of said film.

9. A disposable thermal body pad according to claim 8 wherein said at least one continuous layer comprises a coextruded film having a first side of polypropylene and a second side of ethylene vinyl acetate copolymer, wherein said polypropylene comprises from about 40% to about 60% of the total thickness of said film.

10. The disposable thermal body pad of claim 1 wherein said means for releasably attaching said thermal pad comprises pressure sensitive adhesive.

11. The disposable thermal body pad of claim 10 wherein said means for releasably attaching said thermal body pad being located on said first side of said flexible material so that said second side of said flexible material may be placed directly against a user's body, wherein said first side further comprises an oxygen permeability means.

12. The disposable thermal body pad of claim 11 wherein said unified structure has an upper edge and a lower edge, and wherein said pressure sensitive adhesive is placed in parallel stripes extending continuously from said upper edge to said lower edge between said plurality of heat cells.

13. A disposable thermal body pad according to claim 1 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein said heat cells, when filled with an exothermic composition, have a fill volume to cell volume ratio of from about 0.7 to about 1.0.

14. A disposable thermal body pad according to claim 13 wherein exothermic composition comprises:

a.) from about 30% to about 80% by weight, iron powder;

b.) from about 3% to about 25% by weight, carbonaceous material selected from the group consisting of activated carbon, non-activated carbon, and mixtures thereof;

c.) from about 0.5% to about 10% by weight, metal salt; and d.) from about 1% to about 40% by weight, water.

15. A disposable thermal body pad according to claim 14 wherein said exothermic composition further comprises from about 0.1% to about 30% by weight, of additional water-holding material.

16. A disposable thermal body pad according to claim 13 wherein said exothermic composition comprises:

a.) from about 30% to about 80% by weight, of iron powder;

b.) from about 3% to about 20% by weight, of carbonaceous material selected from the group consisting of activated carbon, non-activated carbon, and mixtures thereof;

c.) from about 0% to about 9% by weight, of an agglomeration aid selected from the group consisting of corn syrup, maltitol syrup, crystallizing sorbitol syrup, amorphous sorbitol syrup, and mixtures thereof; and d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof;

wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and further wherein said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

17. A disposable thermal body pad according to claim 16 wherein said exothermic composition farther comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

18. A disposable thermal body pad according to claim 16 wherein said dry binder comprises from about 4% to about 30% by weight, of microcrystalline cellulose.

19. A disposable thermal body pad according to claim 16 wherein said tablets comprise a geometric shape selected from the group consisting of a disk shape having a hole passing perpendicular to and through the middle of the top and bottom surfaces and a disk shape wherein the top and bottom surfaces are concaved forming a reservoir conducive to holding a liquid.

20. A disposable thermal body pad according to claim 16 wherein said direct compaction articles comprise a density of greater than about 1 g/cm$^3$.

21. A disposable thermal body pad according to claim 1 further comprising additional components selected from the group consisting of active aromatic compounds, non-active aromatic compounds, pharmaceutical actives, and mixtures thereof.

22. A disposable thermal body pad comprising at least one thermal pack having a unified structure comprising at least one continuous layer of material and a plurality of individual heat cells placed into positions fixed within or to said unified structure of said thermal pack which are sufficiently close and relative to each other, so as to block some or all possible axes across said at least one continuous layer, which otherwise would have passed uninterrupted between said heat cells, through said thermal pack, or select regions thereof.

23. A disposable thermal body pad according to claim 22 wherein at least one of said heat cells of four adjacent said heat cells, whose centers form a quadrilateral pattern, blocks one or more of said axes that could otherwise form at least one fold line tangential to the edges of one or more pairings of the remaining said heat cells in the quadrilateral pattern.

24. A disposable thermal body pad according to claim 23 wherein the spacing between said at least one of said heat cells and each of said heat cells of said one or more pairings of said remaining heat cells in said quadrilateral pattern is the same or less than the spacing obtained by dividing the measurement of the smallest diameter of the smallest diameter heat cell of said heat cells within said quadrilateral pattern by 2 and multiplying the result by 0.75.

25. A disposable thermal body pad according to claim 22 wherein at least one of said heat cells of three adjacent said heat cells, whose centers form a triangular pattern, blocks one or more of said axes that could otherwise form at least one fold line tangential to the edges of the remaining pair of said heat cells in the triangular pattern formed by said three heat cells.

26. A disposable thermal body pad according to claim 25 wherein the spacing between said at least one of said heat cells and each of said heat cells of said remaining pair of said heat cells in said triangular pattern is the same or less than the spacing obtained by dividing the measurement of the smallest diameter of the smallest diameter heat cell of said heat cells within said triangular pattern by 2 and multiplying the result by 0.3.

27. A disposable thermal body pad according to claim 22 wherein said at least one continuous layer comprises a semirigid material having a tensile strength of about 0.7 g/mm$^2$, or greater, and at least two-dimensional drape at a temperature of about 25° C., and wherein said material has a tensile strength, at a temperature of about 35° C. or greater, substantially less than said tensile strength of said material at about 25° C.

28. A disposable thermal body pad according to claim 27 wherein said continuous layer comprises a material selected from the group consisting of polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber, synthetic rubber, and mixtures thereof.

29. A disposable thermal body pad according to claim 28 wherein said continuous layer comprises a coextruded material having a first side selected from the group consisting of polyethylene, polypropylene, nylon, polyester, polyvinyl chloride, polyvinylidene chloride, polyurethane, and polystyrene, and a second side selected from the group consisting of saponified ethylene-vinyl acetate copolymer and ethylene-vinyl acetate copolymer.

30. A disposable thermal body pad according to claim 29 wherein said continuous layer comprises a coextruded material having a first side of polypropylene and a second side of ethylene-vinyl acetate copolymer.

31. A disposable thermal body pad according to claim 22 wherein said heat cells comprise a shape selected from the group consisting of a disk, triangle, pyramid, cone, sphere, square, cube, rectangle, rectangular parallelepiped, cylinder, and ellipsoid, said disk having a diameter of from about 1 cm to about 5 cm and a height of from greater than about 0.2 cm to about 1 cm, and said triangle, pyramid, cone, sphere, square, cube, rectangle, rectangular parallelepiped, cylinder, and ellipsoid having a width at its widest point of from about 0.5 cm to about 5 cm and a height at its highest point of from greater than about 0.2 cm to about 1 cm and a length at its longest point of from about 1.5 cm to about 10 cm, and wherein said heat cells, when filled with an exothermic composition, have a fill volume to cell volume ratio of from about 0.7 to about 1.0.

32. A disposable thermal body pad according to claim 31 wherein said exothermic composition comprises:
 a.) from about 30% to about 80% by weight, iron powder;
 b.) from about 3% to about 25% by weight, carbonaceous material selected from the group consisting of activated carbon, non-activated carbon, and mixtures thereof;
 c.) from about 0.5% to about 10% by weight, metal salt; and
 d.) from about 1% to about 40% by weight, water.

33. A disposable thermal body pad according to claim 32 wherein said exothermic composition further comprises from about 0.1% to about 30% by weight, of additional water-holding material.

34. A disposable thermal body pad according to claim 31 wherein said exothermic composition comprises:
 a.) from about 30% to about 80% by weight, of iron powder;
 b.) from about 3% to about 20% by weight, of carbonaceous material selected from the group consisting of activated carbon, non-activated carbon, and mixtures thereof;
 c.) from about 0% to about 9% by weight, of an agglomeration aid selected from the group consisting of corn syrup, maltitol syrup, crystallizing sorbitol syrup, amorphous sorbitol syrup, and mixtures thereof; and
 d.) from about 0% to about 35% by weight, of a dry binder selected from the group consisting of microcrystalline cellulose, maltodextrin, sprayed lactose, co-crystallized sucrose and dextrin, modified dextrose, mannitol, microfine cellulose, pre-gelatinized starch, dicalcium phosphate, calcium carbonate, and mixtures thereof; wherein from about 0.5% to about 10% by weight, of a metal salt selected from the group consisting of alkali metal salts, alkaline earth metal salts, transitional metal salts, and mixtures thereof is added to said composition as part of the dry mix or subsequently in an aqueous solution as brine, and wherein further said exothermic composition comprises a physical form selected from the group consisting of dry agglomerated granules, direct compaction articles, and mixtures thereof, wherein said direct compaction articles are selected from the group consisting of granules, pellets, tablets, slugs, and mixtures thereof, and wherein said tablets and slugs comprise a geometric shape selected from the group consisting of disk, triangle, square, cube, rectangle, cylinder, and ellipsoid, said disk having a diameter of from about 1 cm to about 5 cm and a height of from about 0.08 cm to about 1 cm and said triangle, square, cube, rectangle, cylinder, and ellipsoid having a width at its widest point of from about 0.5 cm to about 5 cm and a height at its highest point of from about 0.08 cm to about 1 cm and a length at its longest point of from about 1 cm to about 10 cm.

35. A disposable thermal body pad according to claim 34 wherein said exothermic composition further comprises from about 0.5% to about 10% by weight, of additional water-holding materials selected from the group consisting of acrylic acid salt starch co-polymer, isobutylene maleic anhydride co-polymer, vermiculite, carboxymethylcellulose, and mixtures thereof.

36. A disposable thermal body pad according to claim 34 wherein said dry binder comprises from about 4% to about 30% by weight, of microcrystalline cellulose.

37. A disposable thermal body pad according to claim 34 wherein said tablets comprise a geometric shape selected from the group consisting of a disk shape having a hole passing perpendicular to and through the middle of the top and bottom surfaces and a disk shape wherein said top and bottom surfaces are concaved forming a reservoir conducive to holding a liquid.

38. A disposable thermal body pad according to claim 34 wherein said direct compaction articles comprise a density of greater than about 1 g/cm³.

39. The disposable thermal body pad of claim 22 wherein said means for releasably attaching said thermal pad comprises pressure sensitive adhesive.

40. The disposable thermal body pad of claim 38 wherein said means for releasably attaching said thermal body pad being located on said first side of said flexible material so that said second side of said flexible material may be placed directly against a user's body, wherein said first side further comprises an oxygen permeability means.

41. The disposable thermal body pad of claim 40 wherein said unified structure has an upper edge and a lower edge, and wherein said pressure sensitive adhesive is placed in parallel stripes extending continuously from said upper edge to said lower edge between said plurality of heat cells.

42. A disposable thermal body pad according to claim 22 further comprising additional components selected from the group consisting of active aromatic compounds, non-active aromatic compounds, pharmaceutical actives, and mixtures thereof.

43. A method of treating body pain, selected from the group consisting of acute muscular, acute skeletal, acute referred, recurrent muscular, recurrent skeletal, recurrent referred, chronic muscular, chronic skeletal, and chronic referred body pain, by applying a disposable thermal body pad of claim 1 to the afflicted body part of a person needing such treatment, to maintain a skin temperature to the afflicted body part of from about 32° C. to about 50° C. for a time period of from about twenty seconds to about twenty-four hours, wherein said skin temperature and said period of time of maintaining said skin temperature is appropriately selected by said person needing such treatment, to substantially relieve said pain without adverse events.

44. A method of treating body pain according to claim 43 wherein said skin temperature is maintained from about 32° C. to about 39° C.

45. A method of treating body pain according to claim 43 wherein said skin temperature is maintained at a temperature of from about 32° C. to about 43° C. for a time period of greater than about 1 hour, wherein said relief of said pain is substantially prolonged for at least about 2 hours after removal of said heat from the afflicted body part of said person needing such treatment.

46. A method of treating body pain according to claim 45 wherein said skin temperature is maintained at a temperature of from about 32° C. to about 41° C. for a time period of greater than about 4 hours, wherein said relief of said pain is substantially prolonged for at least about 1 day after removal of said heat from the back of said person needing such treatment.

47. A method of treating body pain, selected from the group consisting of acute muscular, acute skeletal, acute referred, recurrent muscular, recurrent skeletal, recurrent referred, chronic muscular, chronic skeletal, and chronic referred body pain, by applying a disposable thermal body pad of claim 22 to the afflicted body part of a person needing such treatment, to maintain a skin temperature to the afflicted body part of from about 32° C. to about 50° C. for a time period of from about twenty seconds to about twenty-four hours, wherein said skin temperature and said period of time of maintaining said skin temperature is appropriately selected by said person needing such treatment, to substantially relieve said body pain without adverse events.

48. A method of treating body pain according to claim 47 wherein said skin temperature is maintained from about 32° C. to about 39° C.

49. A method of treating body pain according to claim 47 wherein said skin temperature is maintained at a temperature of from about 32° C. to about 43° C. for a time period of greater than about 1 hour, wherein said relief of said body pain is substantially prolonged for at least about 2 hours after removal of said heat from the afflicted body part of said person needing such treatment.

50. A method of treating body pain according to claim 49 wherein said skin temperature is maintained at a temperature of from about 32° C. to about 41° C. for a time period of greater than about 4 hours, wherein said relief of said body pain is substantially prolonged for at least about 1 day after removal of said heat from the afflicted body part of said person needing such treatment.

* * * * *